US010123991B2

(12) United States Patent
Thompson

(10) Patent No.: US 10,123,991 B2
(45) Date of Patent: Nov. 13, 2018

(54) ELECTROPHILICALLY ENHANCED PHENOLIC COMPOUNDS FOR TREATING INFLAMMATORY RELATED DISEASES AND DISORDERS

(71) Applicant: GLOBAL BIOLIFE INC., Bethesda, MD (US)

(72) Inventor: Daryl Lee Thompson, Winter Haven, FL (US)

(73) Assignee: GLOBAL BIOLIFE INC., Bethesda, MD (US)

( * ) Notice: Subject to any disclaimer, the term of this patent is extended or adjusted under 35 U.S.C. 154(b) by 0 days.

(21) Appl. No.: 15/156,021

(22) Filed: May 16, 2016

(65) Prior Publication Data

US 2016/0331722 A1 Nov. 17, 2016

Related U.S. Application Data

(60) Provisional application No. 62/162,330, filed on May 15, 2015.

(51) Int. Cl.

| | |
|---|---|
| ***A61K 31/352*** | (2006.01) |
| ***A61K 31/7048*** | (2006.01) |
| ***A61K 31/4525*** | (2006.01) |
| ***A61K 9/00*** | (2006.01) |

(52) U.S. Cl.

CPC ........ *A61K 31/352* (2013.01); *A61K 31/4525* (2013.01); *A61K 31/7048* (2013.01)

(58) Field of Classification Search

CPC .............. A61K 31/352; A61K 31/4525; A61K 31/7048

USPC .......................................................... 549/403

See application file for complete search history.

(56) References Cited

U.S. PATENT DOCUMENTS 3,453,282 A 7/1969 Wald
3,495,009 A 2/1970 Tronche
3,689,663 A 9/1972 Josef et al.
4,157,334 A 6/1979 Doria et al.
4,241,069 A 12/1980 Buckler et al.
4,376,781 A 3/1983 Lietti et al.
4,391,603 A * 7/1983 Rosenbaum ........... A61K 8/347 8/405
4,413,004 A 11/1983 Lietti et al.
5,116,954 A 5/1992 Briet et al.
5,399,584 A 3/1995 Ares et al.
5,414,015 A 5/1995 Konoshima et al.
5,702,691 A 12/1997 Ichinose et al.
5,756,538 A 5/1998 Cassels et al.
5,876,703 A 3/1999 Ichinose et al.
6,004,998 A 12/1999 Cassels et al.
6,080,780 A 6/2000 Paladini et al.
6,203,818 B1 3/2001 Vester
6,740,677 B2 5/2004 Xue et al.
7,183,314 B1 2/2007 Xue et al.
7,601,754 B2 10/2009 Caldwell et al.
7,897,637 B2 3/2011 Maher
8,017,649 B2 9/2011 Jarrott et al.
8,022,246 B2 9/2011 Lipton et al.
8,034,838 B2 * 10/2011 Thompson ........... A61K 31/352 514/455
8,680,129 B2 3/2014 Yu
9,296,717 B2 3/2016 Van et al.
9,359,323 B2 6/2016 McPhail et al.
9,616,033 B2 4/2017 Gerk et al.
2007/0116779 A1 5/2007 Mazzio
2008/0044390 A1 2/2008 Jin et al.
2008/0292607 A1 11/2008 Mazzio et al.
2011/0142815 A1 6/2011 Yu
2012/0039796 A1 2/2012 Markou
2012/0115896 A1 5/2012 Bardelli et al.
2012/0213842 A1 * 8/2012 Birbara .................. A61K 8/498 424/443
2014/0294788 A1 10/2014 Bailey et al.
2016/0051536 A1 2/2016 Gerk et al.
2016/0331722 A1 11/2016 Thompson
2016/0367517 A1 * 12/2016 Thompson ........... A61K 31/352

FOREIGN PATENT DOCUMENTS

CN 103012347 * 4/2013
CN 103570695 * 2/2014

(Continued)

OTHER PUBLICATIONS

Chemical Abstracts STN Registry Database record for RN 1211595-42-4, entered on Mar. 19, 2010.*

(Continued)

*Primary Examiner* — Daniel R Carcanague
(74) *Attorney, Agent, or Firm* — Stephen J. Weyer, Esq.; Stites & Harbison, PLLC

(57) ABSTRACT

A therapeutic compound has a modified phenolic compound of the general formula (I)

(I)

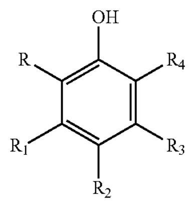

wherein at least one of R, $R_1$, $R_2$, $R_3$, and $R_4$ is an electrophilic group chosen from halogen, aldehyde, haloalkane, alkene, butyryl, flurophenol, sulfonamide, flurophenol sulfoxide and the remaining R, $R_1$, $R_2$, $R_3$, and $R_4$ is are each independently hydrogen, a hydroxyl group, an alkoxy group, a rutinosyl group, a carboxyl group, chromone, benzopyran, a rhamnosyl group, a substituted alkoxy group or a substituted acyloxy group wherein the substituent is chosen from hydroxyl, alkoxy, aryloxy, phenyl, halogen, and amido group. The compound can be used in a therapeutic treatment of inflammatory related diseases and condition.

11 Claims, 12 Drawing Sheets

(56) References Cited

FOREIGN PATENT DOCUMENTS

| | | | |
|---|---|---|---|
| CN | 103570695 | A | 2/2017 |
| CN | 103012347 | A | 5/2017 |
| EP | 3132692 | A1 | 7/1998 |
| WO | WO 2017201042 | A1 | 5/2007 |
| WO | WO 9827970 | A2 | 3/2017 |
| WO | WO 2017053593 | A1 | 11/2017 |

OTHER PUBLICATIONS

Breysse; Chimica Therapeutica 1969, 4, 298-302.*
Binsack; Alcoholism, Clinical and Experimental Research 2001, 25, 434-443.*
Peng; Asian J. Chem. 2014, 26, 4701-4703.*
Kartasasmita; Journal of Applied Sciences 2010, 10, 3098-3104.*
Ichikawa; Organic Preparations and Procedures International 1985, 17, 56-60.*
Gusdinar; Majalah Farmasi Indonesia 2009, 20, 163-169.*
Zhang; Diagnostic Pathology 2014, 9:68, 1-15.*
Bernini; New J. Chem., 2015, 39, 2980-2987. (Year: 2015).*
Daskiewicz; J. Med. Chem. 2005, 48, 2790-2804. (Year: 2005).*
Freitas; European Journal of Medicinal Chemistry 2014, 86, 153-164. (Year: 2014).*
Lu; Environ. Sci. Technol. 2004, 38, 4603-4611. (Year: 2004).*
Marder; Bioorganic & Medicinal Chemistry Letters, 1997, 7, 2003-2008. (Year: 1997).*
Mukai; The Journal of Nutrition 2013, 143, 1558-1564. (Year: 2013).*
Weng; Cancer Metastasis Rev 2012, 31, 323-351. (Year: 2012).*
Polyakov; Chem Nat Compd 1999, 35, 21-28. (Year: 1999).*
Britton; European Journal of Medicinal Chemistry 54 (2012) 952-958. (Year: 2012).*
International Search Report dated Jul. 26, 2017 in International Application No. PCT/US17/32897.
Written Opinion dated Jul. 26, 2017 in International Application No. PCT/US17/32897.
Terao, et al, "Prenylation modulates the bioavailabilty and bioaccumulation of dietary flavonoids", 2014, pp. 12-16, vol. 559, Archives of Biochemistry and Biophysics.
Nair, et al., "Delivery of anti-inflammatory nutraceuticals by nanoparticles for the prevention and treatment of cancer", 2010, pp. 1833-1843, vol. 80 (12), Biochem Phermacol.
PubChem-CID-5281672, create date: Mar. 26, 2005, p. 3 formula.
PubChem-CID-3594, create date Mar. 5, 2005, p. 3 formula.
Polyakov "Chemical modification of the natural flavonoid myricetin", Chemistry of natural compounds 35.1 (1999): 21-28.
Büchter, et al., "Methylated derivatives of myricetin enhance life span in Caenorhabditis elegans dependent on the transcription factor DAF-16", Food & Function 6.10 (2015): 3383-3392.
Rice-Evans, et al. "Structure-antioxidant activity relationships of flavonoids and phenolic acids", Free radical biology and medicine 20.7 (1996): 933-956.
Xue, et al. "Novel myricetin derivatives: Design, synthesis and anticancer activity", European journal of medicinal chemistry 97 (2015): 155-163.
Forbes, et al., "Synthesis and anticancer activity of new flavonoid analogs and inconsistencies in assays related to proliferation and viability measurements", International journal of oncology 45.2 (2014): 831-842.
De, et al., "4'-Hydroxy-3-methoxyflavones with potent antipicornavirus activity", Journal of medicinal chemistry 34.2 (1991): 736-746.

* cited by examiner

EC50: 15.24 μM
CC50: >50 μM

EC50: 0.731 μM
CC50: >250 μM

EC50: 20.82 μM
CC50: >50 μM

EC50: 1.515 μM
CC50: >250 μM

EC50: 49.84 μM
CC50: >50 μM

EC50: 27.68 μM
CC50: >250 μM

EC50: >50 μM

CC50: >50 μM

Cytokine profile in DCs (raw data and graph for 1:50 dilutions can be found in the accompanying Excel file)

Effect of Equivir on Infection with WT Ebola virus in HepG2 Cells

- % EBOV Control (0 Hr)
- % EBOV Control (36 Hr)
- % EBOV Control (72 Hr)
- % Cell Control (36 Hr)
- % Cell Control (72 Hr)

Effect of T-705 on Infection with WT Ebola virus in HepG2 Cells

- % EBOV Control (0 Hr)
- % EBOV Control (36 Hr)
- % EBOV Control (72 Hr)
- % Cell Control (72 Hr)

Effect of Equivir on Infection with WT Ebola virus in THP-1 Cells

- % EBOV Control (0 Hr)
- % EBOV Control (36 Hr)
- % EBOV Control (72 Hr)
- % Cell Control (36 Hr)
- % Cell Control (72 Hr)

Effect of T-705 on Infection with WT Ebola virus in THP-1 Cells

- % EBOV Control (0 Hr)
- % EBOV Control (36 Hr)
- % EBOV Control (72 Hr)
- % Cell Control (72 Hr)

ELECTROPHILICALLY ENHANCED PHENOLIC COMPOUNDS FOR TREATING INFLAMMATORY RELATED DISEASES AND DISORDERS

CROSS REFERENCE TO RELATED APPLICATION

This application claims the benefit of U.S. Provisional patent application Ser. No. 62/162,330, filed on May 15, 2015, herein incorporated by reference.

FIELD OF INVENTION

The present invention relates to a electrophilically enhanced phenolic compounds which include but are not limited to flavonoid compounds and use of these compounds for treating various disorders including disorders which have an inflammatory nexus including inflammatory related diseases and disorders.

BACKGROUND OF THE INVENTION

Metabolic and enzymatic systems of organisms have evolved to incorporate phenolics, phenolic acids, and flavonoids, readily available in the environment from plant food sources, into the associated biochemical pathways of every major metabolic system. Not only do flavonoids have a physiological impact on a multitude of metabolic systems, but they are inherently part of the normal operation of such systems. As part of natural evolution, a flavonoid binding site has been conserved and distributed universally across these pathways. When a chemical reaction is overloaded with reagents, such as excessive glucose, or if there is an impairment of a metabolic component, such as a deformity of a protein, intermediate metabolites build to a concentration which can lead to the dysfunction of the pathway or associated pathways and the expression of a disease condition. A major role of flavonoids is to down and or up regulate certain enzymes to reduce the accumulation of these intermediates, ameliorating their negative effect on the organism.

Because of the distribution of a flavonoid binding site across several pathways, flavonoids have a regulatory impact on several enzymes in systems associated with disease conditions. Most other therapeutics for a disease condition target one to two target enzymes associated with a disease, while the flavonoid targets several.

Disease Classes

There are sixty-four (64) key enzymes distributed across six (6) disease categories. Most drugs used to treat these diseases either down-regulate or up-regulate a target enzyme associated with these diseases.

A listing of each major disease category and the target enzymes associated with such diseases follows.

Cancer

TARGET ENZYMES: Inositol 1,4,5 Triphosphate Kinase (IP3K), Protein Kinase CK2, DNA Topoisomerase II, Mitogen Activated Protein Kinase, CYP 181, Kinase 1 (MEK), MAPK Kinase 4 (MKK4), Glycoxalase, CYP 1A1, Cyclooxygenase, Thioredoxin Reductase, Nuclear Factor Kappa B (NF-Kappa B), Tyrosine Kinase (MET), Extracellular Signal Regulated Kinase (ERK 1-2), HSP 70 ATPase, Xanthine Oxidase, Phostphatidylinositol-3, RAF Kinase, Matrix Metallo Proteinase 1-18, MRP-1, Urokinase, 3-Phosphoglycerate Kinase, Aromatase (CYP-19), X Protein Kinase (XK), Ornithine Decarboxylase (ODC), and Inositol Polyphosphate Multi Kinase (IPMK).

Diabetes and Metabolic Syndrome (Diabetes Mellitus Type 1, Diabetes Mellitus Type 2, Gestational Diabetes, Metabolic Syndrome, Obesity, Glycogen Storage Disorder)

TARGET ENZYMES: Pyruvate Carboxylase, Fatty Acid Synthase, Alpha Amylase, Mitogen Activated Protein Kinase, MAP K (4), Cholesterol Acyl Transferase, Liver Xanthine Oxidase, Glucokinase, Extracellular Regulated Enzyme (ERK), Aldose Reductase, Lipase, Acetyl Co A, Kinase (1), Glucosidase, Angiotensin Converting Enzyme (ACE), 12-Lipo-oxygenase, and HMG-CoA, Kinase (MEK).

Cardiovascular Disease (Hypercholesterolemia, Ischemia, Hypertension, Endocarditis, Myocarditis, Cerebrovascular Disorder, Vascular Permeability, Ischemia)

TARGET ENZYMES: Aceto Acetyl CoA, Squalene Synthase, Oxidosqualene Cyclase, Angiotensin Converting Enzyme, Acetyl CoA, HMG CoA reductase, HMG CoA, and Cholesterol Transferase.

Inflammation and Pain (Acute Pain Disorder, Migraine, Headache, Arthritis, Psoriasis, Asthma, Alcohol Toxicity, Crohn's Disease, Inflammatory Bowel Syndrome, Colitis, Irritated Bowel Syndrome, Rosacea)

TARGET ENZYMES: Glyoxalase 1, Glyoxalase 2, Kinase (1), Polymerase (PARP-1), Mitogen Activated Protein Kinase (MAP K), Nuclear Enzyme Polymerase (ADP Ribose), Caspase 8, MAP K (4), MKK4, Elastase, COX 1, and COX 2.

Neurological Diseases (Alzheimer's Disease, Huntington's Disease, Schizophrenia, Traumatic Brain Injury, Parkinson's)

TARGET ENZYMES: Tyrosine Kinase, Alpha Secretase, Caspase 3, Protease, Beta Site APP Cleaving Enzyme 1 (BACE-1), Kinase (PLK2), Tau Protein Kinase, Beta Secretase, Gamma Secretase, Intercellular Adhesion Molecule 1 (ICAM-1), Glutathione transferase, M(TOR), Dihydrofolate reductase, Serine protease, cysteine protease, Metallo protease, and Aspartic protease.

Virological/Bacteriological Diseases (Human Rhinovirus, Influenza, SARS, MERS, Ebola, Dengue, Malaria, MRSA, Staph, *e. coli*, HIV)

TARGET ENZYMES: Reverse transcriptase, RNA Polymerase (all), Helicase, Topoisomerase, Integrase, Protease (viral budding), Caspase (especially caspase 8), Allantoinase, Dihydroorotase, Butyryl Cholinesterase, and Acetyl Cholinesterase.

Specific Example of One Disease: Diabetes

Type 1 Diabetes (formerly known as Juvenile Diabetes) is characterized by an inability of the body to produce or release insulin. Type 2 Diabetes (also known as Adult Onset Diabetes) is characterized by the body's inability to respond to insulin, or being insulin resistant. Both result in hyperglycemia, often followed by complications such as cardiovascular disease, retinopathy, neuropathy, and nephropathy. Type 1 Diabetes requires the administration of exogenous insulin. Type 2 Diabetes can often be initially controlled by diet alone, but usually requires treatment with antihyperglycemic agents. The most widely prescribed drug for the control of Type 2 Diabetes is the hydrochloride salt of metformin, a biguanide. Such compounds work by inhibiting liver glucose output (gluconeogenesis) and increasing the uptake of glucose by peripheral tissue (such as muscle) by stimulating glucose transporter 4 (GLUT4). A list of drugs and their mode of action is shown in Table 1.

TABLE 1

| CLASS | MODE | AGENT |
|---|---|---|
| sulfonylureas | stimulate insulin release through activation of Ca & K channels | tolbutamide<br>acetohexamide<br>tolazamide<br>chlorpropamide<br>glipizide<br>glyburide<br>glimepiride<br>gliclazide |
| meglitinides | stimulate insulin release through activation of Ca & K channels | repaglinide<br>nateglinide |
| biguanides | inhibit gluconeogenesis, stimulate GLUT4 | metformin<br>phenformin<br>buformin |
| thiazolidinediones | bind to PPARs, regulating adipocyte differentiation, FA & glucose uptake. | rosiglitazone<br>pioglitazone<br>troglitazone |
| α-glucosidase inhibitor | inhibit conversion of starch to glucose | miglitol<br>acarbose |
| GLP analogues/ agonists | bind to GLP receptor, causing insulin release | exenatide<br>liraglutide<br>taspoglutide |
| DPP-4 inhibitors | inhibit degradation of GLP, indirectly causing insulin release | vildagliptin<br>sitagliptin<br>saxagliptin |
| amylin analogues | inhibits gluconeogenesis, gastric enzymes, & gastric emptying | pramlintide |

The leading cause of non-compliance associated with the most widely prescribed antidiabetic drugs is gastro-intestinal discomfort. In particular, α-glucosidase inhibitors and amylin analogues work by slowing or inhibiting the conversion of complex carbohydrates and fats into readily absorbable simpler molecules. This leaves an environment rich in carbohydrates and lipids, readily available to intestinal micro flora. The result is often diarrhea, flatulence, inflammation, and deterioration of the intestinal lining.

Flavonoids have the basic structure:

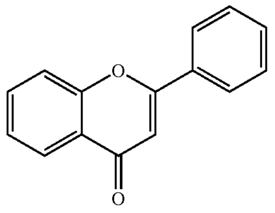 [SMILES: O=c1cc(-c2ccccc2)oc2ccccc12]

and are classified according to IUPC (International Union of Pure and Applied Chemistry) as flavonoids (examples include quercetin and rutin), isoflavonoids (examples include daidzein and genistein), or neoflavonoids (examples include dalbergin and neoflavan).

Flavonoids are effective enzymatic inhibitors or stimulators according to the 1) number of hydroxyl units borne on their phenolic rings, 2) planarity of the molecule, and 3) position of the units on the rings. Planarity and position dictate docking potential. In general, the more hydroxyl units, the more reactive the compound is. At the same time, an increase in reactivity denotes a decrease in stability. The greater the number of hydroxyl units, the more immediate the effect. Fewer units lead to delayed effects. A formulation of flavonoids each with varying numbers of hydroxyl units may be employed as a method to elicit multiple effects. This would be accomplished by alternating ratios of different flavonoids with different numbers and hydroxyl unit orientations.

Scientific literature is replete with the effect of flavonoids on lowering blood glucose via inhibition of α-glucosidase, inhibition of glucose transporter 2 (glucose transport from the gut to the bloodstream), stimulation of glucose transporter 4 (glucose transport from the bloodstream to muscle tissue), stimulation of insulin release, inhibition of gluconeogenesis, inhibition of adipocyte growth and development, stimulation of lipolysis, inhibition of fatty acid synthesis, and increased insulin sensitivity. Flavonoids have been reported to inhibit the activity of *helicobacter pylori*, a major contributor to gastro-intestinal distress, as well as several other flora of the gastro-intestinal tract. In addition, flavonoids show anti-inflammatory activity and support healing of the intestinal lining.

SUMMARY OF THE INVENTION

The present invention relates to electrophilically enhanced phenolic compounds. The electrophilically enhanced phenolic compounds, include but are not limited to, flavonoid compounds. The compounds can be used to treat various disorders including disorders which have an inflammatory nexus including inflammatory related diseases and disorders. One, none limiting example is an electrophilically enhanced myricetin. Electrophilically enhancing such flavonoid increases its binding activity, lowers the Km, thus increasing its efficacy.

In one form a composition includes the addition of an electrophilic moiety via covalent bonding to a phenolic compound such as a flavonoid which elicits an increased docking energy, increasing up or down regulation of enzymes relating to six (6) inflammatory-related disease categories (identified in this disclosure below), and/or increasing the efficacy of a flavonoid over its native state. These compounds advantageously are effective for treating inflammatory related diseases and disorders. These disorders include the above-identified six (6) disease categories which have an inflammatory component, genesis or nexus. The electrophilically enhanced phenolic compounds have a general formula (I)

(I)

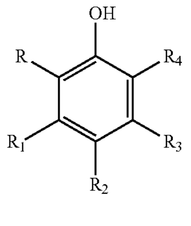

wherein at least one of R, $R_1$, $R_2$, $R_3$, and $R_4$ is an electrophilic group chosen from halogen, aldehyde, haloalkane, alkene, butyryl, flurophenol, sulfonamide, flurophenol sulfoxide and the remaining R, $R_1$, $R_2$, $R_3$, and $R_4$ is are each independently hydrogen, a hydroxyl group, an alkoxy group, a rutinosyl group, a carboxyl group, chromone, benzopyran, a rhamnosyl group, a substituted alkoxy group or a substituted acyloxy group wherein the substituent is chosen from hydroxyl, alkoxy, aryloxy, phenyl, halogen, and amido group. In an advantageous form, the electrophilically enhanced phenolic compound has increased efficacy over its native form when administered to a patient in need of treatment of an inflammatory disease or related disorder.

One example in electrophilically enhanced myricetin in which myricetin is substituted with one or more halogens such as chlorine.

In one advantageous form, $R_1$ is a chromone having the general flavonoid formulas (II) and (II)

Flavanones (II)

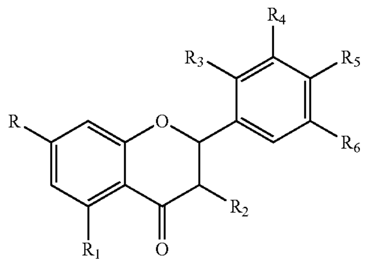

Flavones (III)

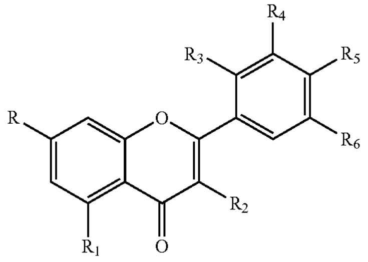

wherein at least one of R, $R_1$, $R_2$, $R_3$, $R_4$, $R_5$, and $R_6$ is an electrophilic group chosen from halogen, aldehyde, haloalkane, alkene, butyryl, flurophenol, sulfonamide, flurophenol sulfoxide and the remaining R, $R_1$, $R_2$, $R_3$, $R_4$, $R_5$, and $R_6$ are each independently hydrogen, a hydroxyl group, an alkoxy group, a rutinosyl group, a rhamnosyl group, a substituted alkoxy group or a substituted acyloxy group wherein the substituent is chosen from hydroxyl, alkoxy, aryloxy, phenyl, halogen, and amido group. In advantageous form, the compound has increased efficacy over its native, non-electrophilically enhanced form, where the enhanced efficacy is based on its ability to treat target diseases and conditions in accordance with this disclosure.

Still in a further form, the flavonoid is selected from compounds derived from 2-phenylchromen-4-one. Still further, in yet an additional embodiment, the flavonoid includes compounds derived from 3-hydroxy-2-phenylchromen-4-one such as, but not limited to, fisiten, galangin, hesperitin, isorhamnetin, kaempferol, myricetin, naringin, quercetin, and rutin.

The present invention, in another form thereof relates to a method for treating inflammatory related diseases which includes administering to a patient in need of treatment therefrom a therapeutically effective amount of a compound of general formula (I). In alternative methods, the treatment may include administering any of the aforementioned specific forms of the general formula (I) including but not limited to those of fisiten, galangin, hesperitin, isorhamnetin, kaempferol, myricetin, naringin, quercetin, and rutin.

In accordance with the present invention, a combination of compounds, myricetin, hesperidin and piperine form a composition known as Equivir. The myricetin can be native or electrophically enhanced.

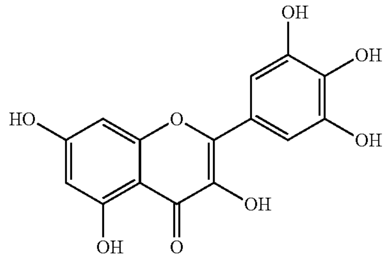

Myricetin

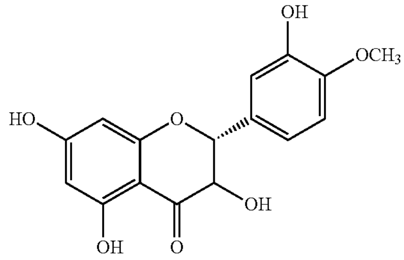

Hesperidin

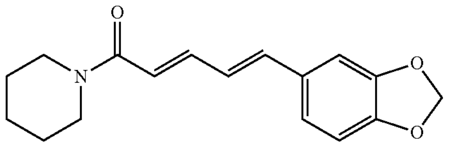

Piperine

Equivir, in accordance with this disclosure has efficacy to treat various disorders, in accordance with this disclosure which include, but are not limited to dengue fever/dengue virus, influenza, rhinovirus, and ebola virus.

DETAILED DESCRIPTION

Figure 1:
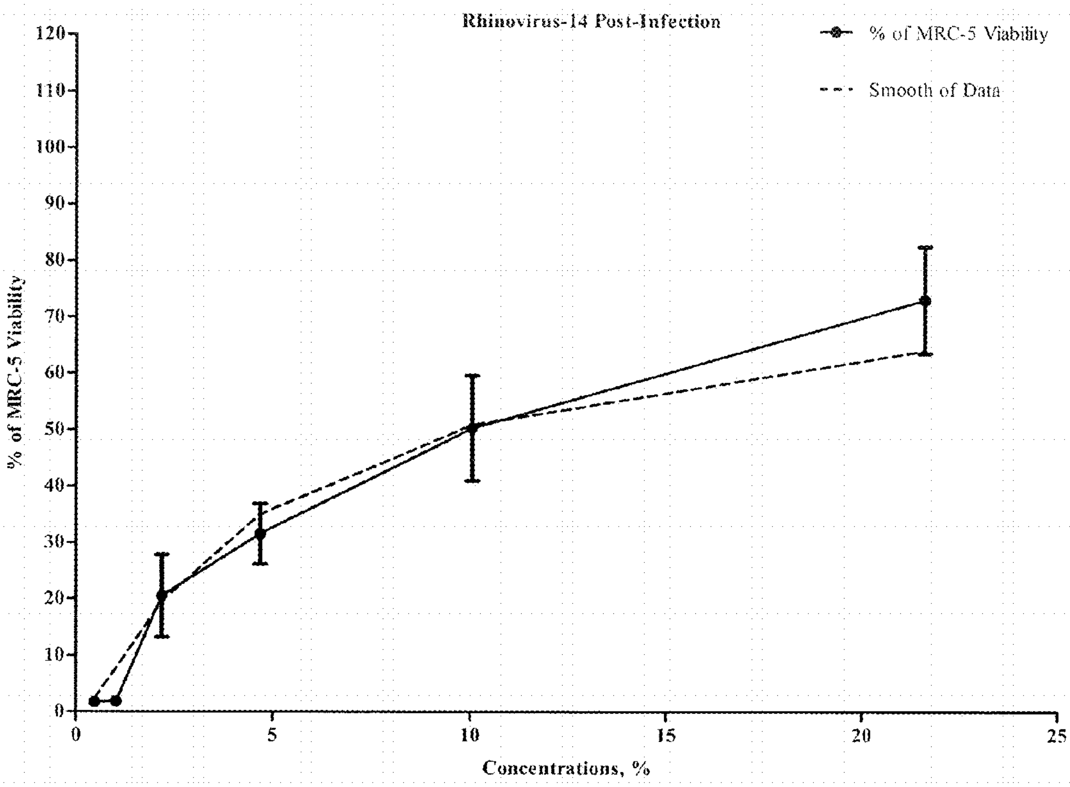
FIG. 1 compares percent of MRC-5 Viability with percent concentration in which percent inhibition of Rhinovirus type 14 is shown following treatment with the test compound, post-infection application.

The present invention will now be described with regard to specific embodiments and exemplar examples to provide a further understanding of the present compound and its use to treat various disorders.

In one advantageous form, a therapeutic compound has a modified phenolic compound of the general formula (I)

(I)

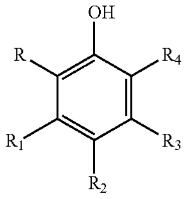

wherein at least one of R, $R_1$, $R_2$, $R_3$, and $R_4$ is an electrophilic group chosen from halogen, aldehyde, haloalkane, alkene, butyryl, flurophenol, sulfonamide, flurophenol sulfoxide and the remaining R, $R_1$, $R_2$, $R_3$, and $R_4$ is are each independently hydrogen, a hydroxyl group, an alkoxy group, a rutinosyl group, a carboxyl group, chromone, benzopyran, a rhamnosyl group, a substituted alkoxy group or a substituted acyloxy group wherein the substituent is chosen from hydroxyl, alkoxy, aryloxy, phenyl, halogen, and amido group, said compound having increased efficacy over its native form.

The therapeutic compound can be used to treat various diseases having an inflammatory component, genesis or nexus including, but not limited to, cancer, diabetic/metabolic syndrome disease conditions, cardiovascular disease, inflammatory/pain, neurological disease, and virological/biological disease conditions.

The therapeutic compound can be formulated as a pharmaceutical composition and may be further modified by a non-evasive systematic dosage form which include but is not limited to a capsule, pill, tablet, specialty tablet (buccal, sublingual, and oral disintegrating), thin film, elixir, liquid solution or suspension, powder, or crystals.

The composition may include a pharmaceutical carrier carried by suitable pharmaceutical carrier which includes any of a series of physical forms and can include a wide variety of pharmaceutically acceptable carriers, diluents and/or excipients that are well known in the art. Accordingly, the suitable pharmaceutical carrier may include solvents, coatings, antibacterial and antifungal agents, isotonic and absorption delaying agents and the like. By "pharmaceutically acceptable" is generally understood to mean that said carrier is substantially compatible with the active ingredient or other ingredients in the composition or formulation and is substantially not deleterious to a patient undergoing treatment thereof. General examples of suitable carriers include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like.

Depending on the nature of the present composition and its formulation, administering the present compound/composition in accordance with this disclosure can be through transmucosal absorption, incorporated into nasal, buccal/sublingual, vaginal, ocular, rectal (suppository, enema), and inhalation (aerosol, inhaler, nebulizer, vaporizer, smoked) applications.

A preferred dose for administering a compound of general formula (I) and a pharmaceutical composition in accordance with the present disclosure is an amount which limits the occurrence of a condition, reduces symptoms associated with the disease condition, and/or prevents the occurrence for a finite time. One of ordinary skill in the art will readily recognize that the amount will vary greatly depending on the nature of the condition of a patient. "An effective amount" or "therapeutically effective amount" of the compound of general formula (I) or a pharmaceutical composition including the compound of general formula (I) in accordance with the present disclosure is intended to mean any non-toxic but sufficient amount of the compound, composition pharmaceutical composition or anything that produces the desired prophylactic or therapeutic effect. Thus, as one of ordinary skill in the art readily understands, the exact amount of the compound, pharmaceutical composition or particular agent that is required will vary from subject to subject depending on the species of the patient, age, and general condition of the subject, severity of the condition being treated, the particular carrier or adjuvant being used and its mode of administration and the like. Similarly, dosing regimen should also be adjusted to suit the patient to whom the composition is administered and will vary again with age, weight, metabolism, etc. of the subject. Therefore, the "effective amount" of any particular compound, composition or agent will vary based on particular circumstances, and an appropriate effect amount may be determined in each case of application by one of ordinary skill in the art using only routine experimentation.

Depending on the nature of the present composition and its formulation, administering the present compound can be through transmucosal absorption, incorporated into nasal, buccal/sublingual, vaginal, ocular, rectal (suppository, enema), and inhalation (aerosol, inhaler, nebulizer, vaporizer, smoked) applications.

A combination of compounds, myricetin, hesperidin and piperine form a composition known as Equivir. Equivir, in accordance with this disclosure has efficacy to treat various disorders in accordance with the present disclosure which include, but are not limited to dengue fever/dengue virus, influenza, rhinovirus, and ebola virus.

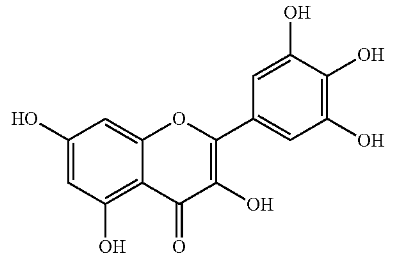

Myricetin

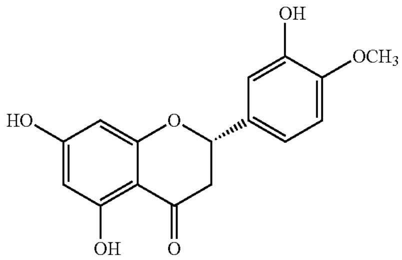

Hesperidin

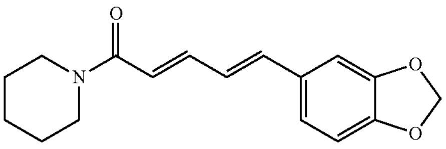

Piperine

A chlorinated flavonoid according to this disclosure can be incorporated into a conventional non-invasive systemic dosage form, such as a capsule, pill, tablet, specialty tablet (buccal, sublingual, oral disintegrating), thin film, elixir, liquid solution or suspension, powder, or crystals. The above dosage forms will also include the necessary physiologically acceptable filler, disintegrants (such as croscarmellose sodium, povidone, crospovidone, sodium starch glycolate, corn starch or microcrystalline cellulose), carrier material, excipient, lubricant (such as magnesium stearate, stearic acid, palmitic acid, calcium stearate, talc, carnauba wax), buffer, antibacterial, bulking agent and/or binder (such as lactose, sugar, gum acacia, corn starch, modified corn starch, polyvinylpyrrolidone, mannitol, sorbitol, inorganic salts such as calcium carbonate and/or cellulose derivatives such as wood cellulose, microcrystalline cellulose, carnauba wax, paraffin, spermaceti, polyethylenes or microcrystalline wax), anti-oxidants (ascorbic acid or sodium bisulfite) or similar.

A chlorinated flavonoid according to this disclosure can be administered by incorporation into a cream, gel, liniment, balm, lotion, ointment, or skin patch.

A chlorinated flavonoid according to this disclosure can be administered through transmucosal absorption, incorporated into nasal, buccal/sublingual, vaginal (douche, pessary), ocular, rectal (suppository, enema), and inhalation (aerosol, inhaler, nebulizer, vaporizer, smoked) applications.

A chlorinated flavonoid according to this disclosure can be administered through intradermal, subcutaneous, intramuscular, intraosseous, intraparitoneal, or intravenous injection.

A chlorinated flavonoid according to this disclosure can be administered through a time-release formulation by incorporating liposomes, drug polymer conjugates, hydrogels, or microspheres.

EXEMPLAR EXAMPLES

The following examples are provided for exemplary purposes to enhance understanding of the present composition and treatment. From the example, one can extrapolate compounds, therapeutic compositions and therapeutic treatments in accordance with the disclosure.

Example 1

According to this disclosure, one or more flavonoids such as for example myricetin, is chlorinated. The compound can be employed individually, or can be combined in a single formulation, for example as a capsule, liquid solution or suspension, syrup, tablet, powder, as well as controlled release formulations.

In a preferred embodiment, 1 to 1000 mg of a chlorinated flavonoid is administered orally in capsule form.

Example 2

A chlorinated flavonoid according to this disclosure can be administered to various mammalian species, such as domesticated animals, horses, cows, sheep, pigs, dogs, cats, humans, etc., in need of such treatment.

The following example is entitled "Non-GLP Evaluation of One Test Compound for Antiviral Activity Versus Rhinovirus 14".

The test product was prepared as follows: 0.312 g of the test product was dissolved in 10 mL DMSO to obtain 100 mM concentration of the test product; 1/1000 dilution of 100 μM test product was prepared in Maintenance Medium to obtain 100 uM concentration; subsequent serial dilutions were made in Maintenance Medium using the progression factor of 2.15. Cytotoxicity of 1/1000 dilution of DMSO in medium was evaluated. A total of eight different concentrations of the test product were evaluated for antiviral properties versus Rhinovirus type 14 strain 1059 (ATCC #VR-284). Post-infection and Pre-infection antiviral activity of the test product was evaluated. Plating was performed in 6 replicates, testing was conducted in duplicate.

Test Methodology:

Test Product: Test Product descriptions are provided in Table 2. Initial Test Product was prepared in DMSO and subsequent concentrations in cell culture medium.

TABLE 2

| Lot Number | Exp. Date | Manufactured Date | Product Name/Description |
|---|---|---|---|
| 1532 | March 2017 | March 2015 | Equivir<br>Myricetin, hesperetin and piperine; small glass vial with black lid containing dark yellow powder |

Virus:

Human Rhinovirus type 14 strain 1059 (ATCC #VR-284).

Virus dose: 0.1 MOI.

Host Cells:

MRC-5 (Human lung fibroblasts, ATCC 11CCL-171).

Medium:

Maintenance Medium—EMEM (ATCC) with 2% Fetal Bovine Serum (Atlas) and Anti-Anti (penicillin-streptomycin-amphotericin B [Gibco]).

MTT Cell Proliferation Assay: ATCC #30-1010K.

Methodology:

The antiviral properties and cytotoxicity were assessed using a Cytopathic Effect (CPE)-based assay. CPE was determined using MTT cell proliferation assay.

Post-infection antiviral activity: Approximately 90% confluent cells were washed with PBS. 100 ul aliquots of 0.1 MOI test virus (medium for the cytotoxicity test) were added to the cells and incubated at 33° C.±2° C. in a $CO_2$ incubator for 1 hour for virus adsorption. After incubation, the virus inoculum was removed; infected cells washed with PBS and overlaid with 100 μl of the test products concentrations. The plates were incubated in a $CO_2$ incubator for 72 hours. Upon completion of incubation, the plates were evaluated for CPE inhibition using MTT assay: cells were washed with PBS; 100 μl of medium and 10 μl of MTT reagent added to each well of the plate; plates were returned to the incubator and incubated for 4 hours at 37° C.±2° C.; following incubation, medium was removed and 100 μl of DMSO added to dissolve purple formazan.

Pre-infection antiviral activity: Approximately 90% confluent cells were washed with PBS. 100 μl aliquots of the test product concentrations were added to the cells and incubated at 37° C.±2° C. in a $CO_2$ incubator for 1 hour. After incubation, 100 μl aliquots of 0.1 MOI test virus were added and incubated at 33° C.±2° C. in a $CO_2$ incubator for 72 hours. Upon completion of incubation, the plates were evaluated for CPE inhibition using MTT assay: cells were washed with PBS; 100 μl of medium and 10 μl of MTT reagent added to each well of the plate; plates were returned to the incubator and incubated for 4 hours at 37° C.±2° C.; following incubation, medium was removed and 100 μl of DMSO added to dissolve purple formazan.

The optical density of the samples was determined using the "VERSAmax" Tunable Microplate Reader (with SOFTmax® PRO Software) set at 570 nm, with blank wells. The results were calculated as percent inhibition of CPE where 100% inhibition of CPE is approximately equal to the mean of the cell control. IC50 values are presented in μM concentrations and were calculated using non-liner regression analysis, GraphPad Prism 5.0 software.

Table 3 presents the summary of inhibitory concentrations.

TABLE 3

Summary for Inhibitory Concentrations of the Test Product versus Rhinovirus type 14 and Toxic Concentrations for MRC-5 Cells

| Test Product Application | IC50, μM Best Fit Value | IC50, μM 95% CI | IC90, μM Best Fit Value | IC90, μM 95% CI | Cytotoxicity, TC50 μM Best Fit Value | Cytotoxicity, TC50 μM 95% CI |
|---|---|---|---|---|---|---|
| Post-Infection | 9.350 | 8.559 to 10.21 | 63.250 | 49.78 to 80.36 | 52.21 | 39.62 to 68.82 |
| Pre-Infection | 549.8 | 332.5 to 909.1 | 206740 | 54522 to 783930 | 52.21 | 39.62 to 68.82 |

Tables 4 and 5, and FIG. 1 present Inhibitory Concentrations (IC) for Post-Infection Application of the Test Product.

TABLE 4

Inhibitory Concentration 50% (1050) for the Post-Infection Product Application (GraphPad Prism 5.0 log(inhibitor) vs. response -- Variable slope (four parameters))

| log(inhibitor) vs. response -- Variable slope (four parameters) | Results |
|---|---|
| Best-fit values | |
| Bottom = | 0.0 |
| Top = | 100.0 |
| LogIC50 | 0.9708 |
| HillSlope | 1.149 |
| IC50 | 9.350 |
| Span = | 100.0 |
| Std. Error | |
| LogIC50 | 0.01923 |
| Hill Slope | 0.06127 |
| 95% Confidence Intervals | |
| LogIC50 | 0.9324 to 1.009 |
| Hil Slope | 1.027 to 1.272 |
| IC50 | 8.559 to 10.21 |
| Goodness of Fit | |
| Degrees of Freedom | 70 |
| R square | 0.9295 |
| Absolute Sum of Squares | 3535 |
| Sy · x | 7.106 |
| Constraints | |
| Bottom | Bottom = 0.0 |
| Top | Top = 100.0 |

TABLE 5

Inhibitory Concentration 90% (IC90) for the Post-Infection Product Application (GraphPad Prism 5.0)

| log(agonist) vs. response - Find ECanything | Results |
|---|---|
| Best-fit values • | |
| logECF | 1.801 |
| HillSlope | 1.149 |
| F = | 90.00 |
| Bottom = | 0.0 |
| Top = | 100.0 |
| ECF | 63.25 |
| Span = | 100.0 |
| Std. Error | |
| logECF | 0.05209 |
| Hi I IS lope | 0.06127 |

TABLE 5-continued

| Inhibitory Concentration 90% (IC90) for the Post-Infection Product Application (GraphPad Prism 5.0) | |
|---|---|
| log(agonist) vs. response - Find ECanything | Results |
| 95% Confidence Intervals | |
| logECF | 1.697 to 1.905 |
| HillSlope | 1.027 to 1.272 |
| ECF | 49.78 to 80.36 |
| Goodness of Fit | |
| Degrees of Freedom | 70 |
| R square | 0.9295 |
| Absolute Sum of Squares | 3535 |
| Sy · x | 7.106 |
| Constraints | |
| F | F = 90.00 |
| Bottom | Bottom = 0.0 |
| Top | Top = 100.0 |
| Number of points | |
| Analyzed | 72 |

Figure 2:
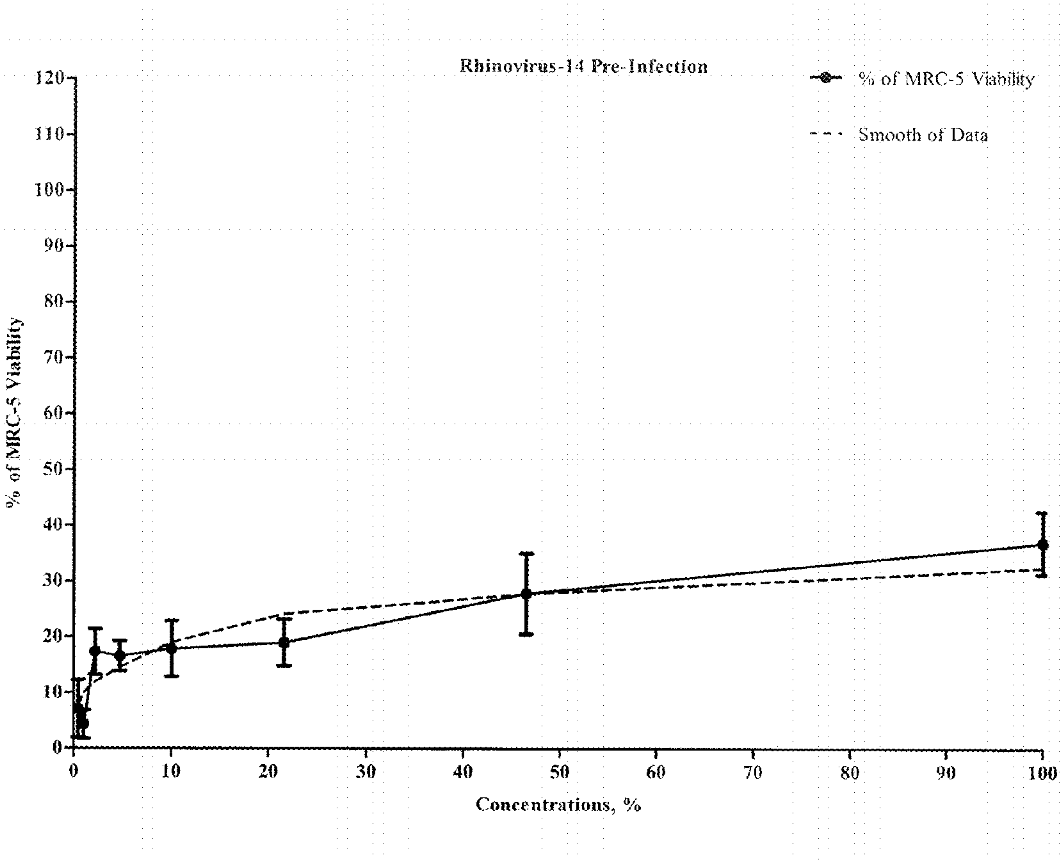
FIG. 2 shows percent inhibition of Rhinovirus type 14 following treatment with the test compound, pre-infection application.

Tables 6 and 7, and FIG. 2 present Inhibitory Concentrations (IC) for Pre-Infection Application of the Test Product.

TABLE 6

| Inhibitory Concentration 50% (IC50) for the Pre-Infection Product Application (GraphPad Prism 5.0 log(inhibitor) vs. response -- Variable slope (four parameters)) | |
|---|---|
| log(inhibitor) vs. response -- Variable slope (four parameters) | Results |
| Best-fit values | |
| Bottom = | 0.0 |
| Top = | 100.0 |
| LogIC50 | 2.740 |
| HillSlope | 0.3705 |
| 1050 | 549.8 |
| Span = | 100.0 |
| Std. Error | |
| LogIC50 | 0.1098 |
| HillSlope | 0.02695 |
| 95% Confidence Intervals | |
| Log1C50 | 2.522 to 2.959 |
| HillSlope | 0.3170 to 0.4241 |
| 1050 | 332.5 to 909.1 |
| Goodness of Fit | |
| Degrees of Freedom | 94 |
| R square | 0.7303 |
| Absolute Sum of Squares | 3011 |
| Sy · x | 5.660 |
| Constraints | |
| Bottom | Bottom = 0.0 |
| Top | Top = 100.0 |

TABLE 7

| Inhibitory Concentration 90% (IC90) for the Pre-Infection Product Application (GraphPad Prism 5.0) | |
|---|---|
| log(agonist) vs. response -- Find ECanything | Results |
| Best-fit values | |
| logECF | 5.315 |
| HillSlope | 0.3705 |
| F = | 90.00 |
| Bottom = | 0.0 |
| Top = | 100.0 |
| ECF | 206740 |
| Span = | 100.0 |
| Std. Error | |
| logECF | 0.2911 |
| HillSlope | 0.02095 |
| 95% Confidence Intervals | |
| logECF | 4.737 to 5.894 |
| HillSlope | 0.3170 to 0.4241 |
| ECF | 54522 to 783930 |
| Goodness of Fit | |
| Degrees of Freedom | 94 |
| R square | 0.7303 |
| Absolute Sum of Squares | 3011 |
| Sy · x | 5.660 |
| Constraints | |
| F | F = 90.00 |
| Bottom | Bottom = 0.0 |
| Top | Top = 100.0 |
| Number of points | |
| Analyzed | 96 |

Figure 3:
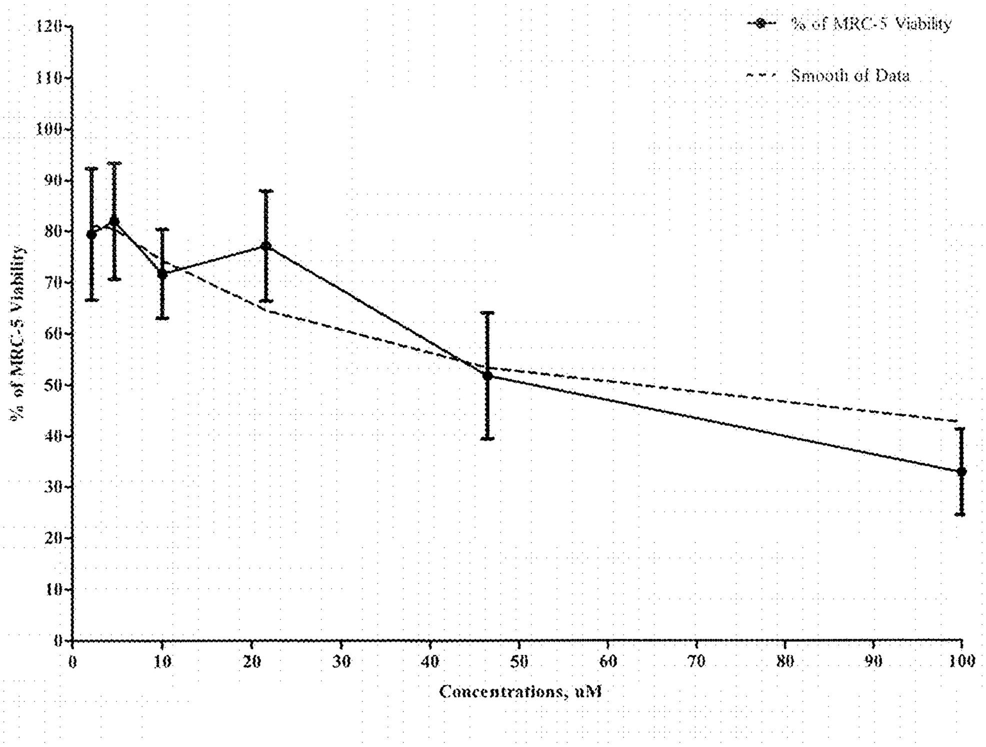
FIG. 3 is a chart showing percent of MRC-5 viability following treatment with the test compound.
Figure 4:
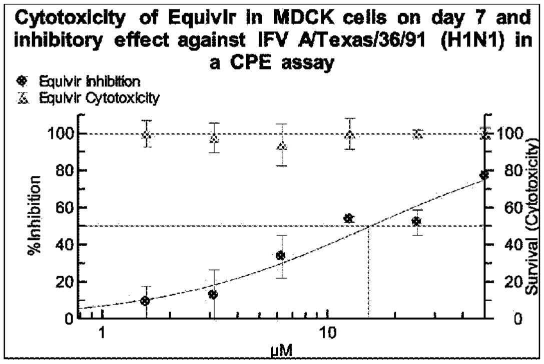
FIG. 4 shows cytotoxicity of Equivir in MDCK cells on day 7 and inhibitory effect against IFVA/Texas/36/91 (H1N1) in a CPE assay.
Figure 5:
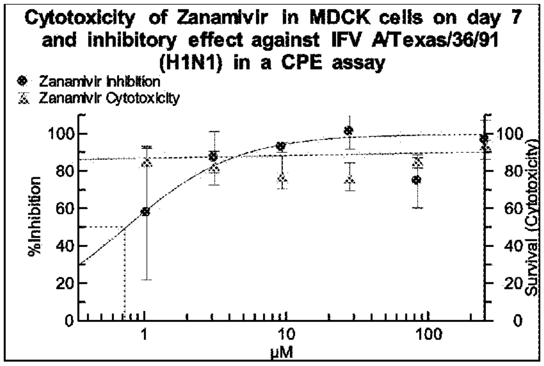
FIG. 5 depicts a toxicity of Zanamivir IR in MDCK cells on day 7 and inhibitory effect against IFV A/Texas/36/91 (H1N1) in a CPE assay.
Figure 6:
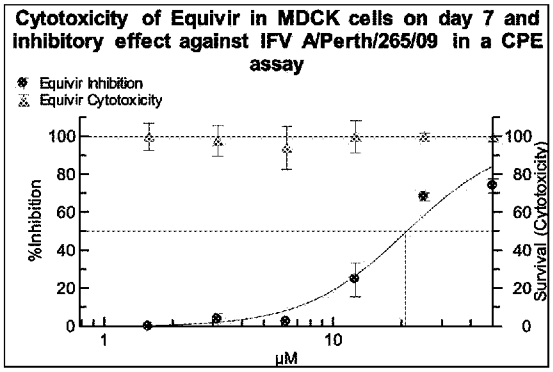
FIG. 6 shows the cytotoxicity of Equivir in MDCK cells on day 7 and inhibitory effect against IFV A/Perth/265/09 in a CPE assay.
Figure 7:
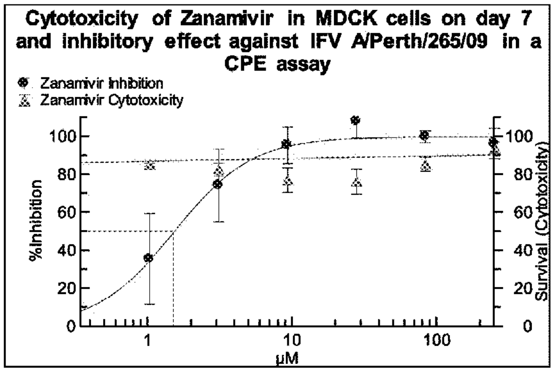
FIG. 7 is a graph showing cytotoxicity of Zanamivir in MDCK cells on day 7 and inhibitory effect against IFV A/Perth/265/09 in a CPE assay.
Figure 8:
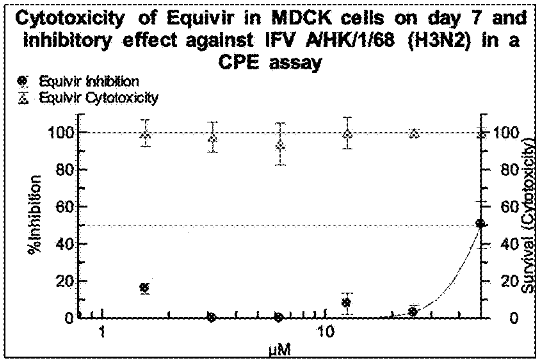
FIG. 8 is a graph showing cytotoxicity of Equivir in MDCK cells on day 7 and inhibitory effect against IFV A/HK/1/68 (H3N2) in a CPE assay.
Figure 9:
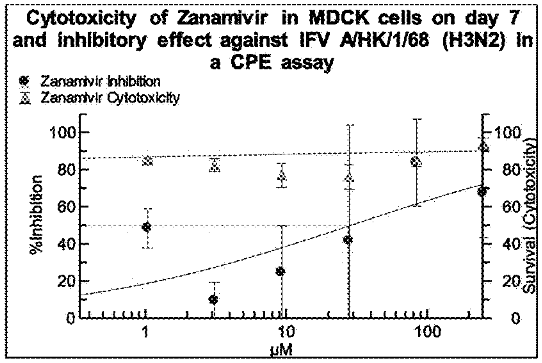
FIG. 9 is a graph showing cytotoxicity of Zanamivir in MDCK cells on day 7 and inhibitory effect against IFV A/HK/1/68 (H3N2) in a CPE assay.

Table 8 and FIG. 3 present Toxic Concentration 50% (TC50) for the MRC-5 cells.

TABLE 8

| Toxic Concentration 50% (TC50) for the MRC-5 cells | |
|---|---|
| log(inhibitor) vs. response -- Variable slope (four parameters) | Results |
| Best-fit values | |
| Bottom = | 0.0 |
| Top = | 100.0 |
| LogIC50 | 1.718 |
| HillSlope | −0.6397 |
| IC50 | 52.21 |
| Span = | 100.0 |
| Std. Error | |
| LogIC50 | 0.06005 |
| HillSlope | 0.06918 |
| 95% Confidence Intervals | |
| LogIC50 | 1.598 to 1.838 |
| HillSlope | −0.7778 to −0.5016 |
| IC50 | 39.62 to 68.82 |
| Goodness of Fit | |
| Degrees of Freedom | 70 |
| R square | 0.6226 |
| Absolute Sum of Squares | 11512 |
| Sy · x | 12.82 |
| Constraints | |
| Bottom | Bottom = 0.0 |
| Top | Top = 100.0 |

Example 3

Analysis Of Equivir Against Influenza Virus And Dengue Virus

The following example and experiment had the following goals:

- Determine the antiviral activity of Equivir against three influenza A viruses in a CPE assay:
- A/TX/36/91 (H1N1)
- A/Perth/265/09 (H1N1) and
- A/HK/1/68 (H3N2);
- Determine cytotoxicity in MDCK cells on day 7;
- Determine antiviral activity against DENV-2 New Guinea C in dendritic cells (yield reduction assay); and
- Determine cytokine profile (IFN-γ, IL-1β, IL-2, IL-4, IL-6, IL-8, IL-10, IL-12p70, IL-13 and TNF-α) in dendritic cells after infection (MSD).

TABLE 9

| | Efficacy overview EC50[μM] | | | |
|---|---|---|---|---|
| | A/TX/36/91 | A/Perth/265/09 | A/HK/1/68 | DENV-2 |
| Equivir | 15.24 | 20.82 | 49.84 | >50 |
| Zanamivir | 0.731 | 1.515 | 27.68 | N/A |

Data for influence of virus in MDCK cells.

Data is shown in FIGS. 4-8 relating to influenza virus in MDCK cells.

CPE-based EC50 assay.

The following experiment was conducted as follows:

- Cells were seeded in 96-well plates and incubated overnight.
- The next day serial dilutions of the test article (starting at 50 μM, 2 fold dilutions) as well as a control compound were prepared in medium.
- The growth medium was aspirated from the cells and the compound dilutions were added for a one-hour incubation period.
- Afterwards the virus was added at an MOI of 0.01 and the cells were incubated for 7 days.
- The cells were then fixed and stained with crystal violet in glutaric dialdehyde solution.
- The optical density was determined and the EC50 was calculated using the uninfected (cells only) control as 0% CPE and the controls without compound (virus only) as 100% CPE using a 4-PL curve fit of the OD.

Cytotoxicity assay

Cytotoxicity was tested as follows. Cells were seeded in black-walled 96-well plates and incubated overnight. The next day serial dilutions of the test article were prepared. The growth medium was aspirated from the cells and the compound dilutions were added. Cells that were incubated with medium only were used for 0% cytotoxicity data. Medium was aspirated and cells were lysed for evaluation of the ATP content using Promega's CelltiterGlo kit (MDCK cells: day 7). The resulting luciferase luminescence was quantified and used to calculate the CC50 using a 4-PL curve fit.

Dengue Virus in Dendritic Cells

Figure 10:
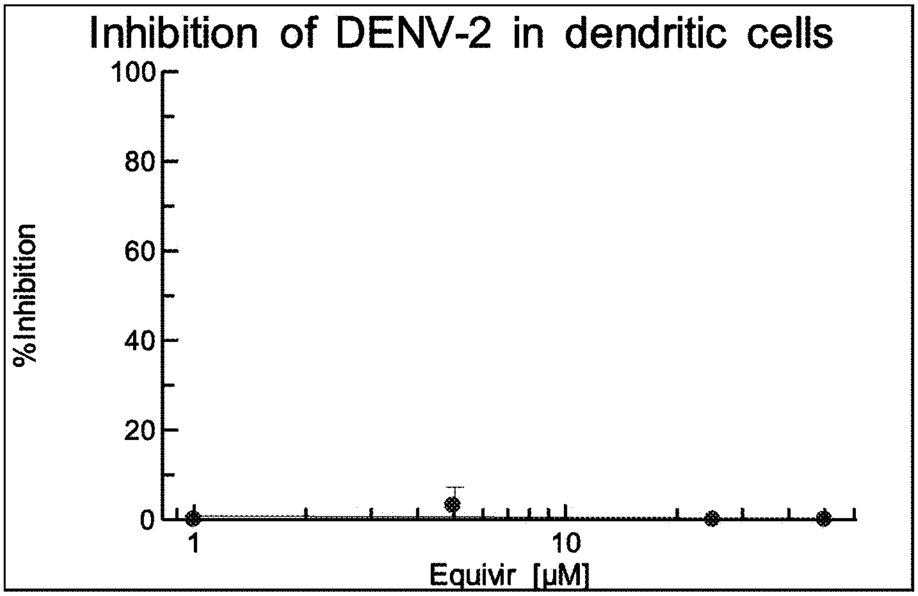
FIG. 10 is a chart showing inhibition of DENV-2 in dendritic cells.

Dengue virus was determined in the following experiment in dendritic cells with data shown in FIG. 10.

The following summarizes the experiment conducted.

Differentiation of Monocytes

Purified, frozen monocytes were received from one donor. Differentiation initiated with GM-CSF and IL-4 in three flasks. Harvest, infection, and characterization occurred after 7 days.

Dendritic Cell Characterization

Figure 11:
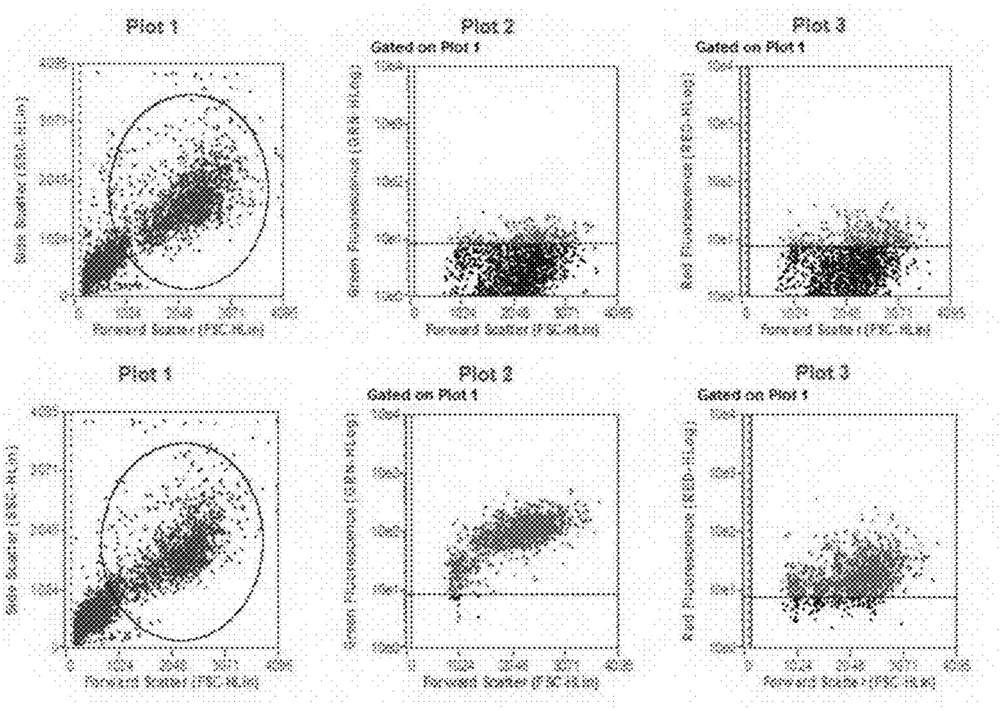
FIG. 11 comprises a series of six panels directed to dendritic cell characterization in accordance with the present invention.

The following characterization was performed with results shown in panels A-F of FIG. 11.

- Non-adherent cells (DCs) were counted to $7.0\times10^6$
- Recovered DCs showed the characteristic profile Infection of DC with DENV-2

The following experiment was conducted as follows:

- $5\times10^5$ of freshly harvested cells were infected with DENV-2 New Guinea C at M011.0 for 2 hours at 37° C.
- Following infection, the cells were washed and compound dilutions (50, 25, 5, and 1 μM) were added in duplicate.
- Supernatants were harvested after 2 days and titrated in an immunoplaque assay. Immunoplaque Assay.

The following experiment was conducted as follows:

- Vero cells were seeded in 24-well plates at $1\times10^5$ cells per well and allowed to adhere overnight.
- Supernatants were diluted 10-fold starting at 1:100.
- Vero cells were infected and incubated for 1 h at 37° C.
- After incubation 1 mL of 0.8% methylcellulose was added to each well.
- Cells were fixed and plaques were detected after 4 days.
- After the incubation period the overlay was removed and the cells were fixed with methanol/ethanol.
- Foci of infection were detected with an antibody against DENV E protein and stained with an HRP substrate.
- Plaques were counted and the EC50 was calculated based on a 4-PL curve fit.

Cytokine Profile

In order to determine cytokine profile, the following was conducted.

MSD

Figure 12:
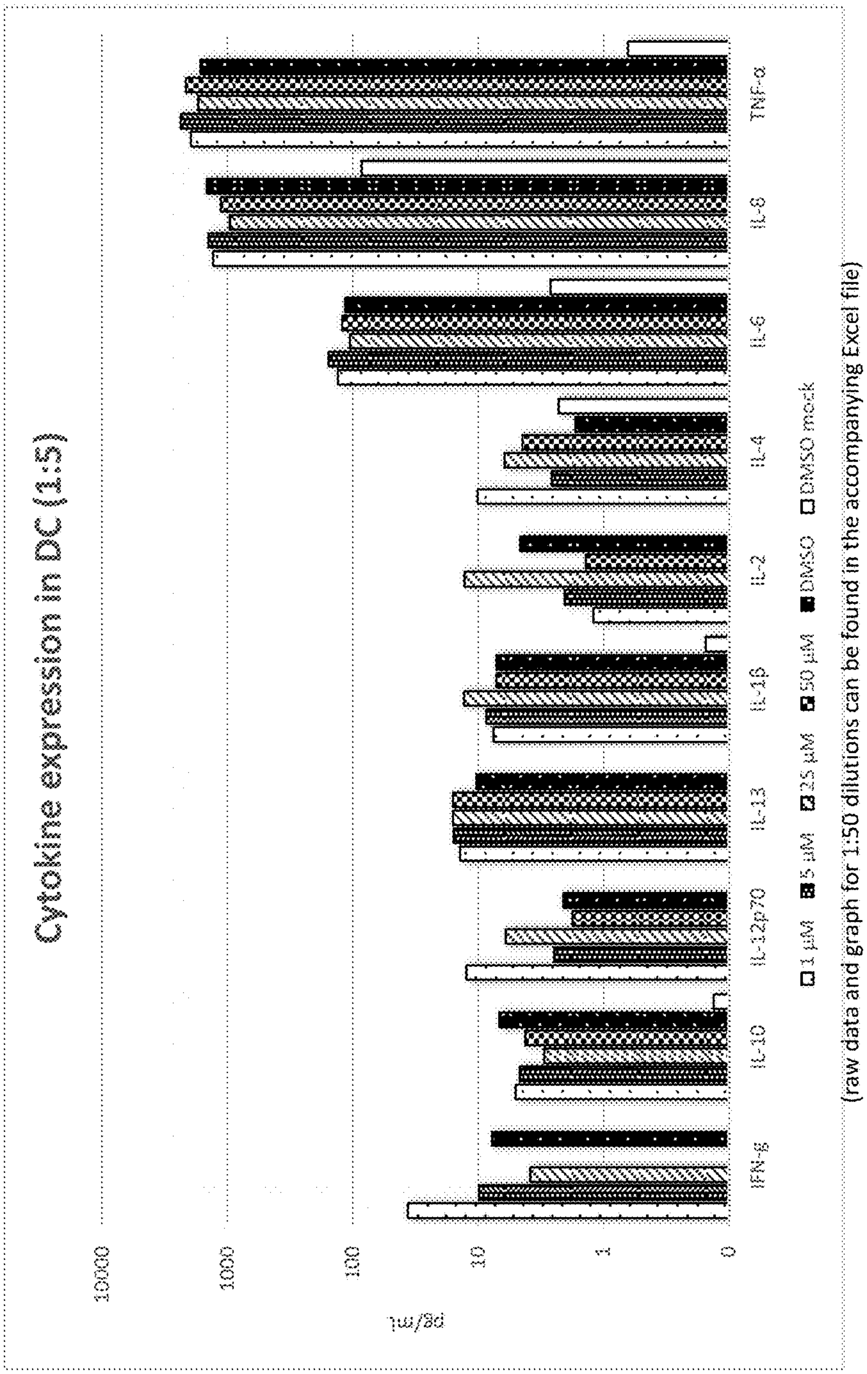
FIG. 12 is a chart showing cytokine profile in DCs.
Figure 13:
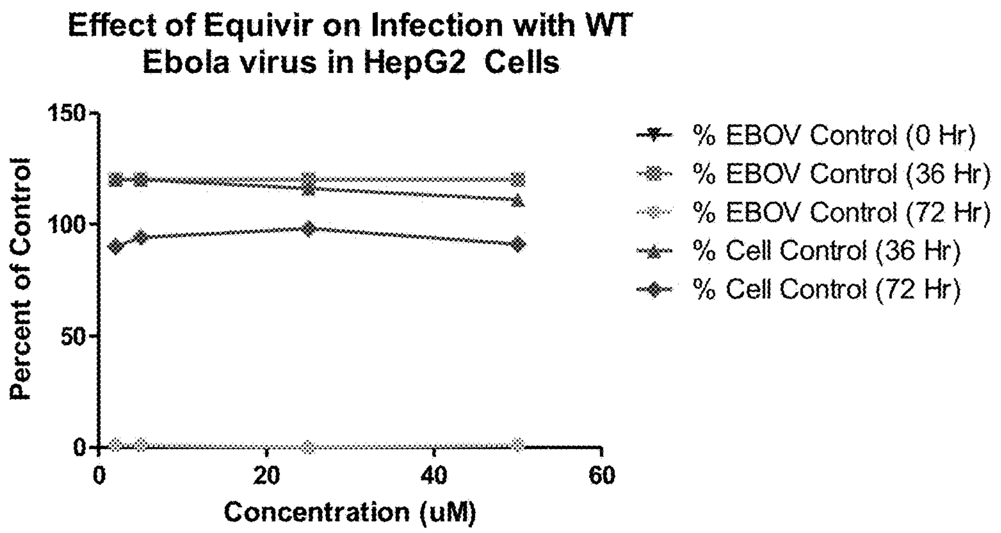
FIG. 13 is a chart showing the effect of Equivir on Infection with WT Ebola virus in HepG2 cells.
Figure 14:
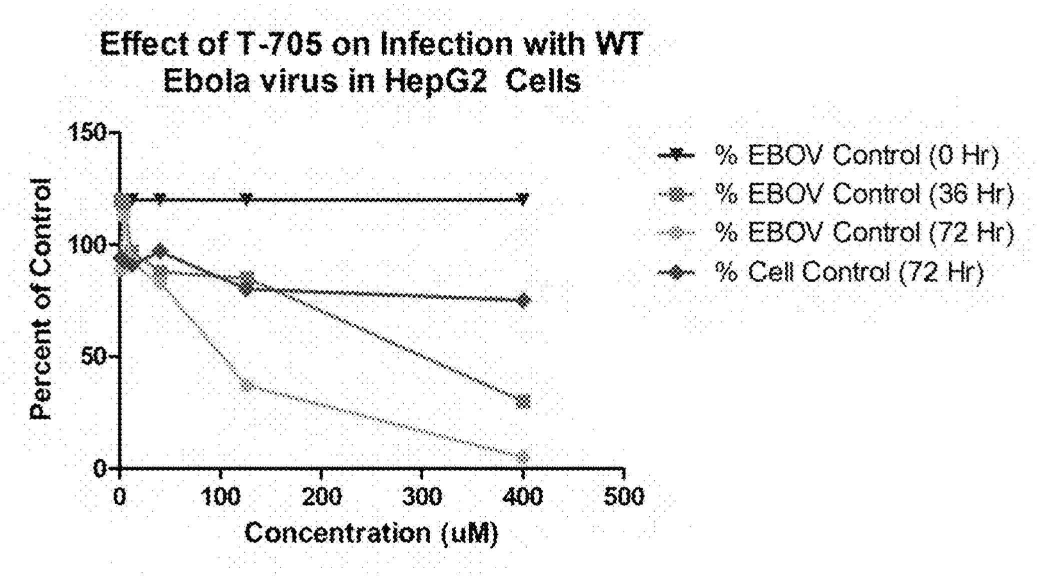
FIG. 14 is a chart showing the effect of T-705 on Infection with WT Ebola virus in HepG2 cells.
Figure 15:
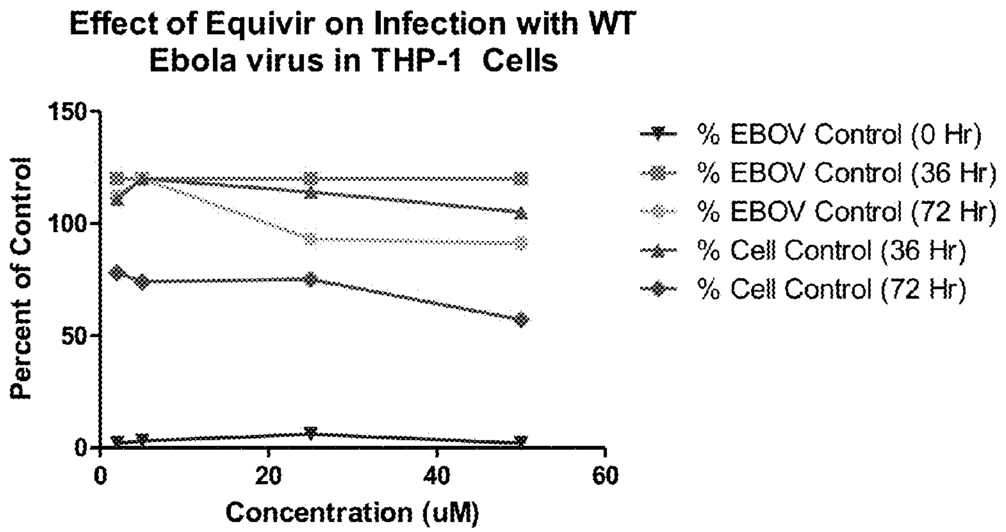
FIG. 15 is a chart showing the effect of Equivir on infection with WT Ebola virus in THP-1 cells.
Figure 16:
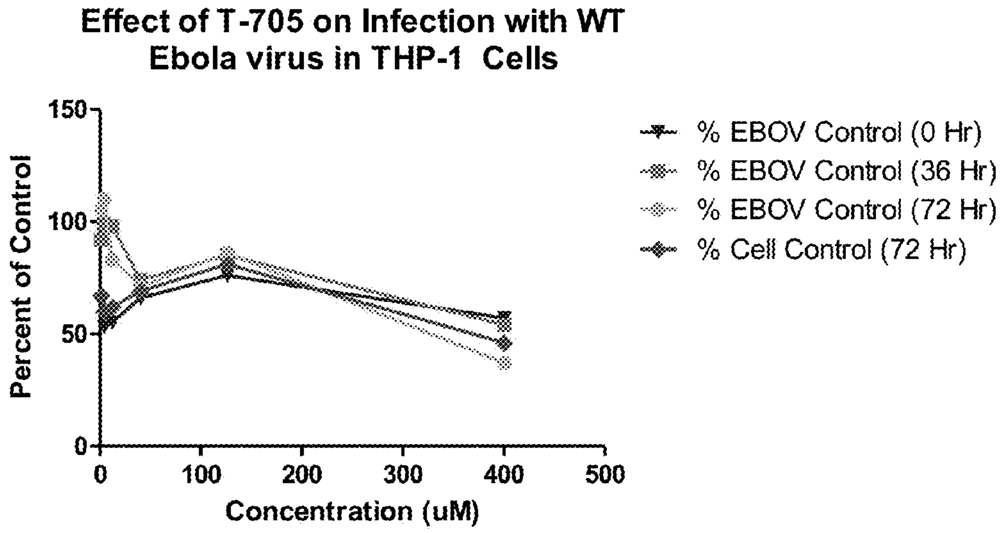
FIG. 16 is a chart showing the effect of T-705 on infection with WT Ebola virus in THP-1 cells.
Figure 17:
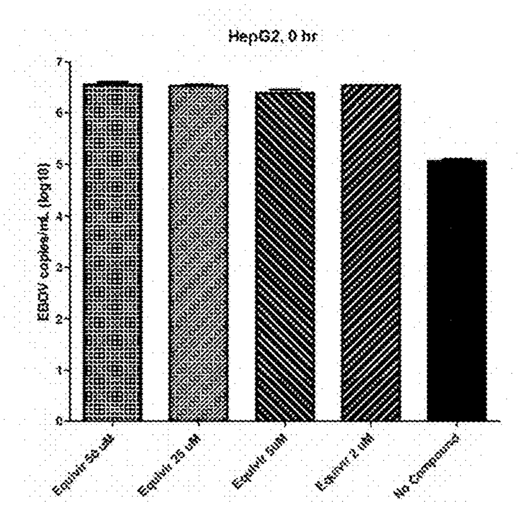
FIG. 17 is a chart with experimental data for anti-EBOV activity in HepG2 shown at zero hours.
Figure 18:
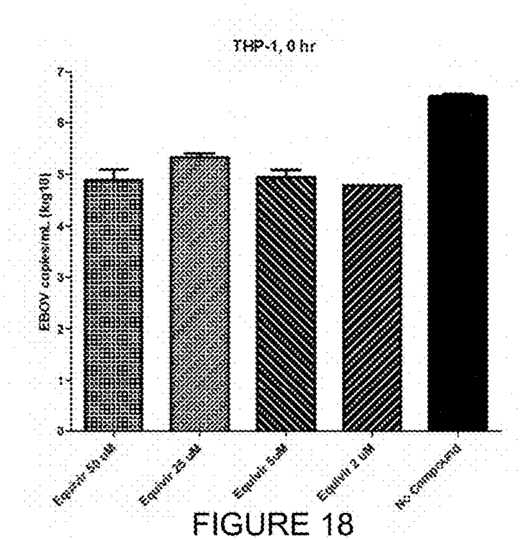
FIG. 18 is a chart with experimental data for anti-EBOV activity in THP-1 shown at zero hours.
Figure 19:
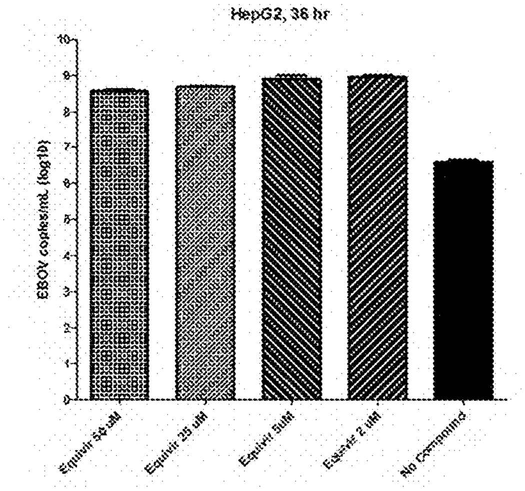
FIG. 19 is a chart with experimental data for anti-EBOV activity in HepG2 shown at 36 hours.
Figure 20:
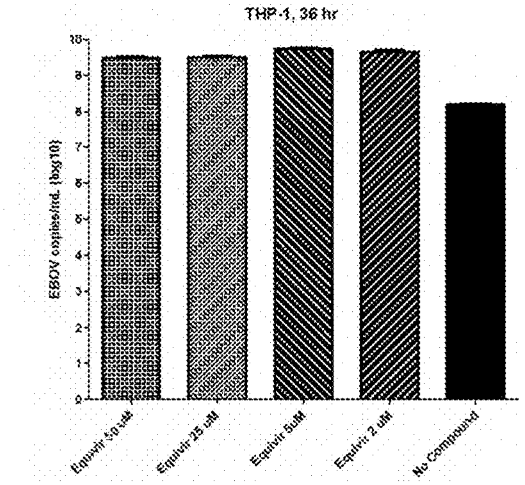
FIG. 20 is a chart with experimental data for anti-EBOV activity in THP-1 shown at 36 hours.
Figure 21:
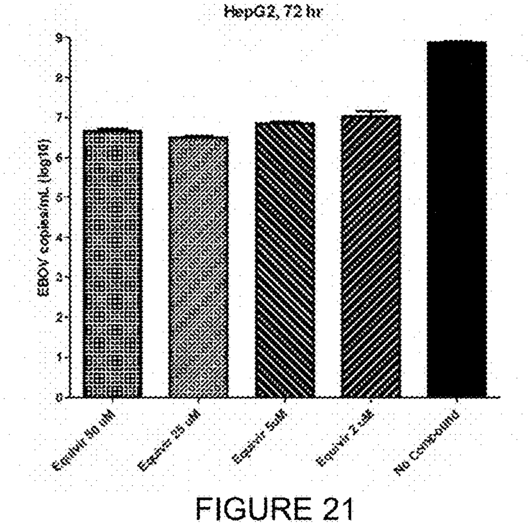
FIG. 21 is a chart with experimental data for anti-EBOV activity in HepG2 cells, shown at 72 hours.
Figure 22:
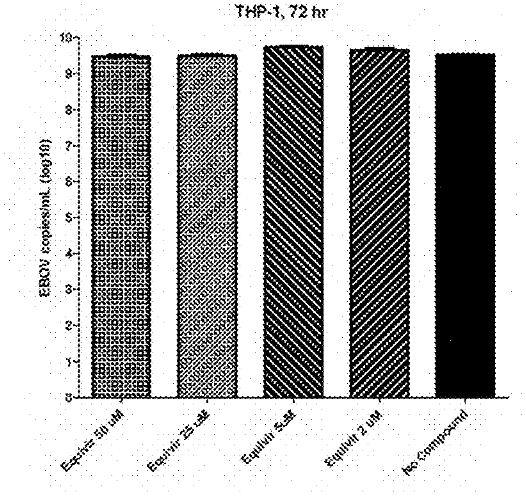
FIG. 22 is a chart with experimental data for anti-EBOV activity in THP-1 shown at 72 hours.

The following characterizes the experiment for MSD as follows:

- Supernatants from dendritic cells were diluted 1:5 and 1:50 and analyzed for levels of IFN-γ, IL-10, I L-2, Iβ L-4, I L-6, I L-8, IL-10, IL-12p70, IL-13 and TNF-α using MSD human proinflammatory kit 1 plates.
- Data was plotted against concentration of Equivir.
- The cytokine profile in DCs is shown in a graph in FIG. 12.

It now will be clear in view of the following disclosure including experiments and examples that the present compound including Equivir have enhanced properties in terms of efficacy in treating inflammatory diseases including but not limited to influenza, dengue virus and ebola. This enhanced property of the present compound is relative to prior known compounds including prior know flavonoids.

Example 4: Ebola Virus Screening Assay

The following experiments demonstrate efficacy in treatment of Ebola.

The goal of these experiments are to evaluate the antiviral efficacy, cytotoxicity, and effect on cytokine response of one (1) Global Research and Discovery Group compound, Equivir, against Ebola virus (EBOV) in HepG2 and THP-1 cells.

Drug Preparation

Equivir was prepared as a pre-solubilized stock. The solubilized stocks were stored at 4° C. until the day of assay. The stocks were thawed at room temperature on the day of assay setup and used to generate the working drug dilutions used in the assays. The compound was evaluated in the assays using a 4 different testing concentrations (50 μM, 25 μM, 5 μM and 2 μM). EBOV inhibitor T-705 was used as the positive control using a 400 μM high-test concentration with 5 additional serial half-log dilutions (concentration range=1.26 μM to 400 μM).

Description of the EBOV Antiviral Testing by Yield Reduction Assay

For the yield reduction assay, HepG2 and THP-1 cells maintained in Modified Eagle's medium (MEM) with 10% fetal bovine serum (FBS), and 1× GlutaMax were plated in 24-well plates. The confluent monolayer was infected with EBOV at a MOI of 0.1 for 1 hour at 37° C. with rocking every 15 minutes. Following infection, medium containing virus was removed and plates washed three times with PBS to remove residual virus. Following washing, the test article was added in the medium at 4 concentrations in duplicate and plates were incubated at 37° C. for 72 hours. Medium was collected at 0, 36 and 72 hours post-infection for assessment by real time RT-PCR to determine the EBOV genome equivalents compared to a viral RNA standard. Additionally, the effect on cytokine response was evaluated using the ProcartaPlex immunoassay kit (cat. no. EPX180-12165-901, eBioscience, San Diego, Calif.). EBOV inhibitor T-705 was used as the positive control and a media only negative control (no virus) and virus only control (no compound) was included.

Cell Preparation

HepG2 and THP-1 cells were obtained from ATCC and were routinely passaged in T-75 flasks using standard tissue culture techniques based on the specifications provided by the supplier. On the day preceding the assays, the cells were split 1:2 to assure they were in an exponential growth phase at the time of infection. Total cell number and percent viability determinations were performed using a hemacytometer and trypan blue exclusion. Cell viability must be greater than 95% for the cells to be utilized in the assay. For the yield reduction assay, the cells were added to 24-well plates in a volume of 100 μL. For cytotoxicity assays, the cells were added to 96-well plates in a volume of 100 μL on the day preceding the assay.

Virus Preparation

The virus used for this assay is Zaire ebola virus strain 199510621. For each assay, a pre-titered aliquot of virus was removed from the freezer (−80° C.) and allowed to thaw slowly to room temperature in a biological safety cabinet in a BSL-4 laboratory. The virus was diluted in tissue culture medium and 100 lit added to each well (approximate MOI of 0.1).

Cytotoxicity Analysis

The test articles were added to cells at 4 concentrations in quadruplicate and plates were incubated at 37° C. for 36 and/or 72 hours. Toxicity plates also contain cell control wells (cells only) and drug colorimetric control wells (drug only). At assay termination, the assay plates were stained with the soluble tetrazolium-based dye MTS (CellTiter®96 Reagent, Promega) to determine cell viability and quantify compound toxicity. MTS is metabolized by the mitochondrial enzymes of metabolically active cells to yield a soluble formazan product, allowing the rapid quantitative analysis of cell viability and compound cytotoxicity. This reagent is a stable, single solution that does not require preparation before use. At termination of the assay, 10-25 μL of MTS reagent was added per well (10% final concentration based on volume) and the microtiter plates were then incubated for 4-6 hours at 37° C., 5% $CO_2$ to assess cell viability. Adhesive plate sealers were used in place of the lids, the sealed plate was inverted several times to mix the soluble formazan product and the plate was read spectrophotometrically at 490/650 nm with a Molecular Devices SpectraMax i3 plate reader.

Cytokine Analysis

The effect on cytokine response was evaluated using the ProcartaPlex immunoassay kit (cat. no. EPX180-12165-901, eBioscience, San Diego, Calif.) according to the manufacturer's instructions. This assay detects the following antigens: IL-12, IL-23, IL-27, GM-CSF, IFN gamma, IL-1beta, IL-10, IL-13, IL-17A, IL-18, IL-2, IL-21, IL-22, IL-4, IL-5, IL-6, IL-9, and TNF alpha. A no compound control (virus only) and media only (no virus) control was included in the analysis for comparison. The assay was read on a Luminex instrument and the results analyzed with the ProcartaPlex Analyst Software 1.0.

Results

A summary of the results from experiments preformed are provided in Tables 10 and 11 below and with data shown in FIGS. 13-22.

Equivir showed the most antiviral activity against EBOV in THP-1 cells at 0 hours post-infection and in HepG2 cells at 72 hours post-infection. Overall the compound was not toxic in HepG2 or THP-1 cells. The T-705 control worked as expected in HepG2 cells, but was not as active in THP-1 cells. Most of the cytokines evaluated were below the lower limit of quantitation of the assay and therefore the interpretation of the results were inconclusive.

TABLE 10

Activity of GRDG Compound Against EBOV in He G2 Cells

| Compound ID | High-Test Concentration | % EBOV Copies Control 0 Hour | 36 Hour | 72 Hour | % Cell Control 36 Hour | 72 Hour |
|---|---|---|---|---|---|---|
| Equivir | 50 μM | 120 | 120 | 1 | 111 | 91 |
| | 25 μM | 120 | 120 | 0 | 116 | 98 |
| | 5 μM | 120 | 120 | 1 | 120 | 94 |
| | 2 μM | 120 | 120 | 1 | 120 | 90 |
| T-705 | 400 μM | 120 | 30 | 5 | ND | 75 |
| | 126 μM | 120 | 85 | 37 | ND | 80 |
| | 40 μM | 120 | 88 | 83 | ND | 97 |
| | 12 μM | 120 | 97 | 92 | ND | 91 |
| | 4 μM | 120 | 118 | 113 | ND | 93 |
| | 1.26 μM | 120 | 120 | 89 | ND | 94 |

ND—Not Done

TABLE 11

Activity of GRDG Compound Against EBOV in THP-1 Cells

| Compound ID | High-Test Concentration | % EBOV Copies Control 0 Hour | 36 Hour | 72 Hour | % Cell Control 36 Hour | 72 Hour |
|---|---|---|---|---|---|---|
| Equivir | 50 μM | 2 | 120 | 91 | 105 | 57 |
| | 25 μM | 6 | 120 | 93 | 114 | 75 |
| | 5 μM | 3 | 120 | 120 | 120 | 74 |
| | 2 μM | 2 | 120 | 112 | 111 | 78 |
| T-705 | 400 μM | 57 | 54 | 37 | ND | 46 |
| | 126 μM | 76 | 85 | 86 | ND | 81 |
| | 40 μM | 66 | 74 | 71 | ND | 69 |
| | 12 μM | 55 | 98 | 83 | ND | 62 |
| | 4 μM | 53 | 99 | 110 | ND | 60 |
| | 1.26 μM | 64 | 92 | 105 | ND | 67 |

ND—Not Done

Discussion

Equivir, was evaluated for antiviral efficacy against EBOV in HepG2 and THP-1 cells. The experimental data and graphical results obtained from these assays are included as in FIGS. 13-22. Equivir was active against EBOV in THP-1 cells at 0 hours post-infection and in HepG2 cells at 72 hours post-infection. It appears that Equivir has an immediate antiviral effect at the early time point in THP-1 cells, but as the virus replicates the effect is lost. In contrast, Equivir is active against EBOV in HepG2 cells at the later time point. This activity was observed for all concentrations evaluated in both cell lines. Overall these results provide evidence that Equivir is active against EBOV. Further testing should be completed to confirm these results and determine a dose response.

The overall assay performance was validated by the control compound T-705, which exhibited the expected levels of antiviral activity in the assay using HepG2 cells. However, the control compound was not as active as expected in THP-1 cells. THP-1 cells are not the standard cell line used for this assay and these results indicate that further optimization of a control compound is needed. Most of the cytokines evaluated were below the lower limit of quantitation of the assay and therefore the interpretation of the results were inconclusive.

One of ordinary skill in the art will recognize that additional embodiments are also possible without departing from the teachings of the presently-disclosed subject matter. This detailed description, and particularly the specific details of the exemplary embodiments disclosed herein, is given primarily for clarity of understanding, and no unnecessary limitations are to be understood therefrom, for modifications will become apparent to those skilled in the art upon reading this disclosure and can be made without departing from the spirit and scope of the presently-disclosed subject matter.

What is claimed is:

1. A compound having a general flavonoid formula

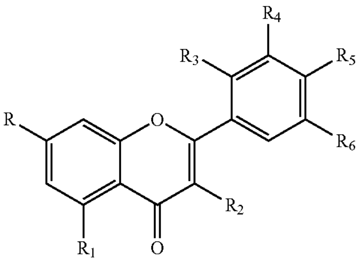

wherein R, $R_1$, $R_2$, $R_4$, $R_5$, and $R_6$ are a hydroxyl group or chlorine, $R_3$ is hydrogen; and wherein, at least one of R, $R_1$, $R_2$, $R_4$, $R_5$, and $R_6$ is chlorine.

2. The compound of claim 1 wherein at least two of R, $R_1$, $R_2$, $R_4$, $R_5$, and $R_6$ are chlorine.

3. The compound of claim 1 having the formula of:

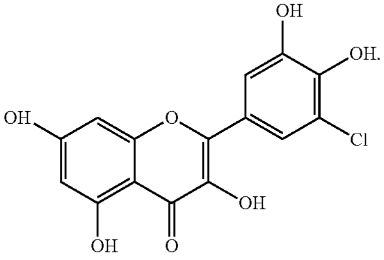 [SMILES: O=c1c(O)c(-c2cc(O)c(O)c(Cl)c2)oc2cc(O)cc(O)c12]

4. The compound of claim 1 having the formula of:

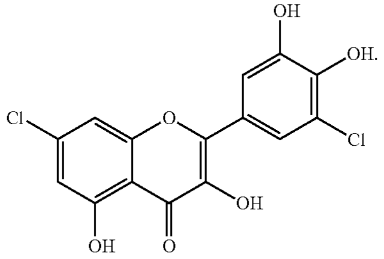 [SMILES: O=c1c(O)c(-c2cc(O)c(O)c(Cl)c2)oc2cc(Cl)cc(O)c12]

5. The compound of claim 1, wherein one of R, $R_1$, $R_2$, $R_4$, $R_5$, and $R_6$ is chlorine.

6. The compound of claim 1, wherein two of R, $R_1$, $R_2$, $R_4$, $R_5$, and $R_6$ are chlorine.

7. A method of treating a viral infection comprising administering a therapeutically effective amount of the compound of claim 1 to a patient in need of treatment therefrom.

8. A pharmaceutical composition comprising the compound of claim 1 incorporated into a conventional non-invasive systemic dosage form.

9. The pharmaceutical composition of claim 8, wherein the non-invasive systemic dosage form is selected from the group consisting of a capsule, pill and tablet.

10. A method of treating a viral infection comprising administering to a patient in need of treatment therefrom, a therapeutically effective amount of the pharmaceutical composition of claim 8.

11. The method of claim 10 wherein the compound is further in combination with hesperidin and piperine.

* * * * *